United States Patent
Zilberman et al.

(10) Patent No.: US 11,707,270 B1
(45) Date of Patent: Jul. 25, 2023

(54) ARTHROSCOPIC TOOL FOR LABRUM REPAIR PROCEDURE AND A METHOD FOR USE THEREOF

(71) Applicant: T.A.G. Medical Products Corporation Ltd., Kibbutz Gaaton (IL)

(72) Inventors: Roy Zilberman, Qadarim (IL); David Morgensteren, Rosh HaAyin (IL); Hagay Sitry, Haifa (IL); Hagay Botansky, Haifa (IL)

(73) Assignee: T.A.G. Medical Products Corporation Ltd., Kibbutz Gaaton (IL)

( * ) Notice: Subject to any disclaimer, the term of this patent is extended or adjusted under 35 U.S.C. 154(b) by 0 days.

(21) Appl. No.: 16/275,415

(22) Filed: Feb. 14, 2019

Related U.S. Application Data (60) Provisional application No. 62/631,571, filed on Feb. 16, 2018.

(51) Int. Cl.
*A61B 17/04* (2006.01)
*A61B 17/17* (2006.01)

(52) U.S. Cl.
CPC ...... *A61B 17/0401* (2013.01); *A61B 17/1742* (2013.01); *A61B 17/0482* (2013.01); *A61B 17/1778* (2016.11); *A61B 17/1796* (2013.01); *A61B 2017/0409* (2013.01)

(58) Field of Classification Search
CPC ............ A61B 17/0401; A61B 17/1742; A61B 17/1778; A61B 17/0482; A61B 17/1796; A61B 2017/04
See application file for complete search history.

(56) References Cited

U.S. PATENT DOCUMENTS

| | | | |
|---|---|---|---|
| 2011/0166579 A1* | 7/2011 | Deem | A61F 2/30 606/90 |
| 2012/0116408 A1* | 5/2012 | Torrie | A61B 17/1746 606/91 |
| 2013/0066371 A1* | 3/2013 | Rogers | A61F 2/4601 606/232 |
| 2013/0172997 A1* | 7/2013 | Euteneuer | A61F 2/0805 623/13.11 |
| 2017/0143328 A1* | 5/2017 | Overes | A61B 17/0482 |

* cited by examiner

*Primary Examiner* — George J Ulsh (57) ABSTRACT

An arthroscopic tool for labrum repair procedure, including: a cannulated working channel having a proximal end and a distal end; and a holding element adapted to be attached to the proximal end of the working channel for supporting a labrum during an arthroscopic labrum repair procedure.

32 Claims, 11 Drawing Sheets

Fig. 8B ows # ARTHROSCOPIC TOOL FOR LABRUM REPAIR PROCEDURE AND A METHOD FOR USE THEREOF

RELATED APPLICATION/S

This application claims the benefit of priority under 35 USC § 119(e) of U.S. Provisional Patent Application No. 62/631,571 filed on Feb. 16, 2018, the contents of which are incorporated by reference as if fully set forth herein in its entirety.

FIELD AND BACKGROUND OF THE INVENTION

The present invention generally relates to tools for labrum repair procedure, for example arthroscopic tools for hip reconstruction procedure.

Treatment of musculoskeletal disease typically involves reattachment of ligaments, tendons or other tissue to a bone. This requires placement of anchors within the bone. Following insertion of the anchor, the tissue to be repaired is captured by a suture, the suture is pre-attached to the anchor, tension is adjusted, and then the suture is often knotted so that the tissue is secured in a desired position.

In particular, various structural hip abnormalities require hip reconstruction procedures, which involve disattachment of the labrum tissue. The labrum then has to be re-attached to the bone using anchors with sutures. Treatment of the hip joint is especially challenging, since the hip joint is deep, delivery of surgical instruments into the joint space while still allowing control of the surgical instrument from outside the patient's body can be challenging. Additionally, the working space in the hip joint is minimal and thus there is little room for repairing the joint, such as when reattaching a torn labrum to the acetabular rim.

SUMMARY OF THE INVENTION

The present invention seeks to provide an improved arthroscopic tool for labrum repair procedure.

There is thus provided in accordance with an embodiment of the present invention, an arthroscopic tool for labrum repair procedure, including a cannulated working channel having a proximal end and a distal end, and a holding element adapted to be attached to the proximal end of the working channel for supporting a labrum during an arthroscopic labrum repair procedure.

Preferably, the tool for labrum repair procedure also includes an anchor cassette adapted to be attached to the working channel.

Further preferably, the anchor cassette includes at least two anchors, which are linked together by a surgical suture.

BRIEF DESCRIPTION OF THE SEVERAL VIEWS OF THE DRAWINGS

The present invention will be understood and appreciated more fully from the following detailed description, taken in conjunction with the drawings in which.

DESCRIPTION OF SPECIFIC EMBODIMENTS OF THE INVENTION

A tool for labrum repair procedure is disclosed herein, which is particularly useful for attaching a soft tissue to a bone, such as for example attachment of the labrum to the acetabular bone or attachment of a labrum to the glenoid bone.

Figure 1A:
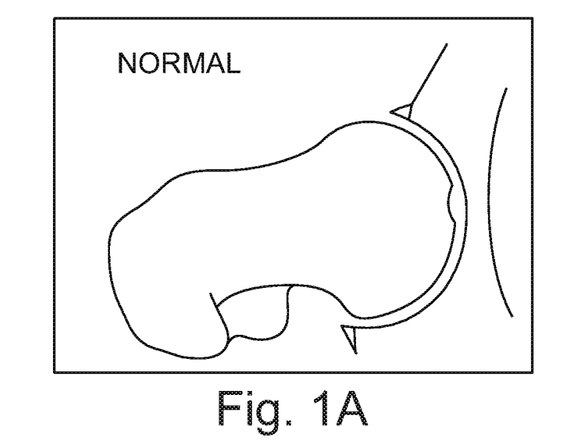
FIGS. 1A-1D are simplified illustration of typical anatomical structures of the hip joint.
Figure 1B:
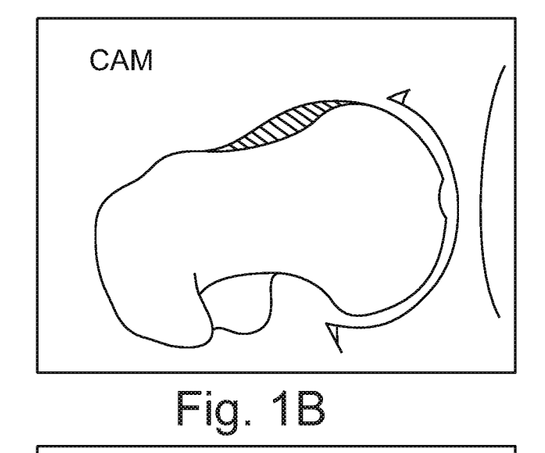
Figure 1C:
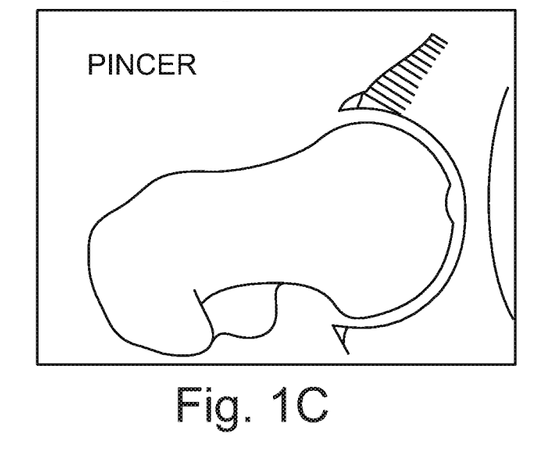
Figure 1D:
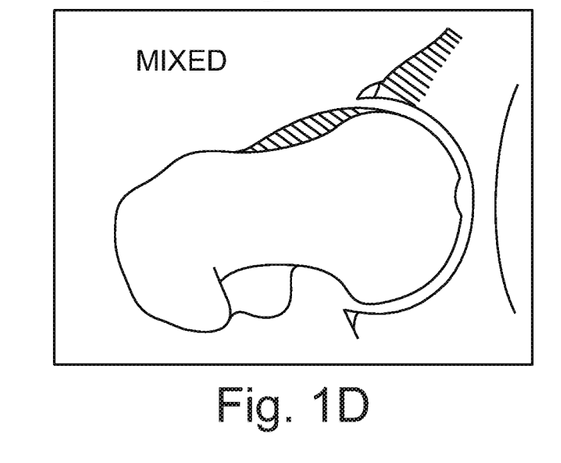

Reference is now made to FIGS. 1A-lD, which illustrate typical anatomical structures of the hip joint. A normal hip joint structure is seen in FIG. 1A, where the femoral bone is partially inserted into the acetabular bone. A pathological structure of the hip joint is seen in FIG. 1B, where the femoral bone is enlarged and thus the hip joint is prevented from proper functioning. An additional pathological structure of the hip joint is seen in FIG. 1C, where the acetabular bone is enlarged and thus the hip joint is prevented from proper functioning. Yet additional pathological structure of the hip joint is seen in FIG. 1D, where both the femoral and the acetabular bone is enlarged and thus the hip joint is prevented from proper functioning.

The surgical procedure currently known in the art involves partially detaching the labrum, which is disposed between the femoral and the acetabular bone, from the bone, repairing the pathological bone structure and then re-attaching the labrum to the bone using sutures that encircle the labrum in order to attach it to the bone. It is known that sutures disposed around the labrum are traumatic for the patient and can cause difficult healing or wear of the joint.

It is a particular feature of an embodiment of the present invention that the suture is passed through the labrum instead of encircling the labrum, thus providing for easier healing and proper functioning of the hip joint.

It is appreciated that similar surgical procedure may be performed on a labrum disposed between the glenoid and the humerus head bone of the shoulder joint.

Figure 2:
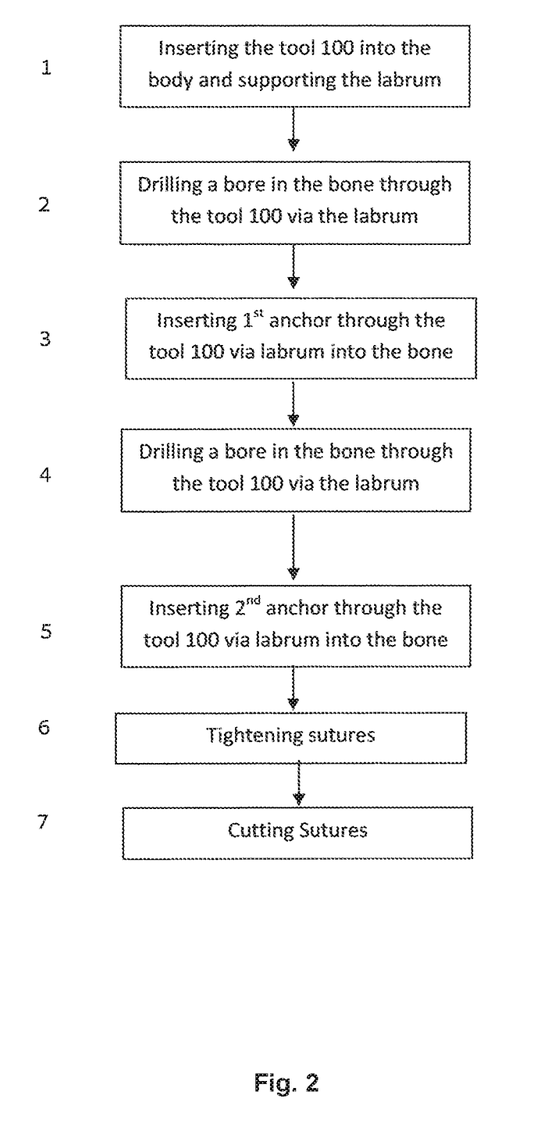
FIG. 2 is a simplified flow chart illustrating a surgical procedure for labrum repair procedure.

Reference is now made to FIG. 2, which is a simplified flow chart illustrating a surgical procedure for labrum repair procedure.

As seen in FIG. 2, a tool 100 constructed and operative in accordance with an embodiment of the present invention is inserted into the body of a patient and is adapted to support the labrum. A bore is drilled in the bone through the tool 100 via the labrum, using drilling element, such as K-wire for example.

It is a particular feature of an embodiment of the present invention that the tool 100 is used as a working channel for various surgical tools, such as a drill, a pusher, suture passer, suture cutter.

It is further seen in FIG. 2 that a $1^{st}$ anchor is inserted through tool 100 via the labrum into the bone of the patient. An additional bore is drilled in another location in the bone of a patient. Further, a $2^{nd}$ anchor is inserted through tool 100 via the labrum into the additional bore in the bone of the patient. It is appreciated that any desired number of anchors may be inserted into the bone of the patient in order to securely attach the labrum to the bone. It is appreciated that each anchors has a suture attached thereto.

It is appreciated that at least four anchors are used during a single procedure, thus steps 2-7 of the procedure are repeated as required.

Following insertion of the desired number of anchors, the sutures of the anchors are tightened and the residual suture material is cut.

It is a particular feature of an embodiment of the present invention that all steps of the procedure are performed without removing the tool 100 from the initial insertion site, thus enabling the surgeon to perform the entire procedure through a single working channel and obviating the need for re-locating the treatment site following each step in the procedure. The tool 100 preferably operatively engages the labrum during various stages of the procedure.

Figure 3A:
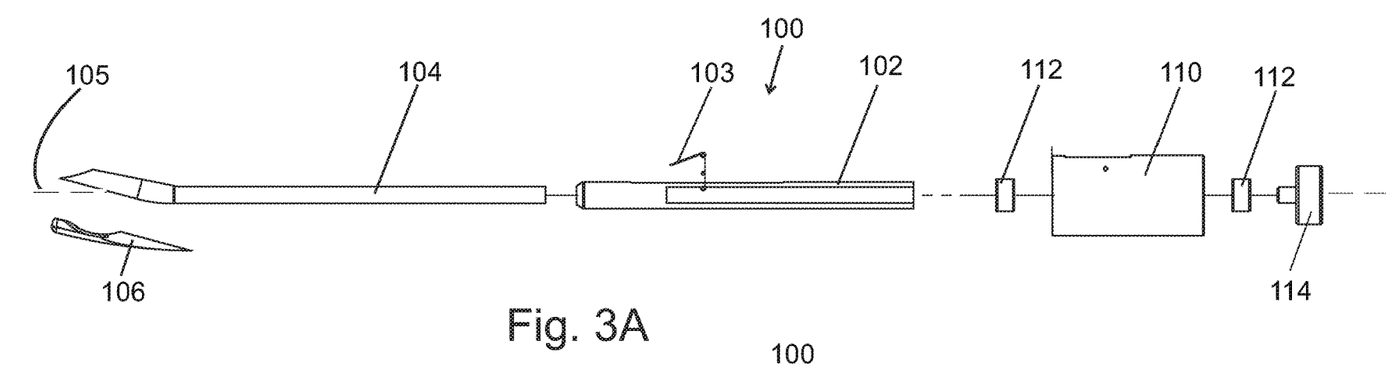
FIGS. 3A & 3B are simplified exploded and sectional exploded views respectively of a tool for labrum repair procedure constructed and operative in accordance with an embodiment of the present invention.
Figure 3B:
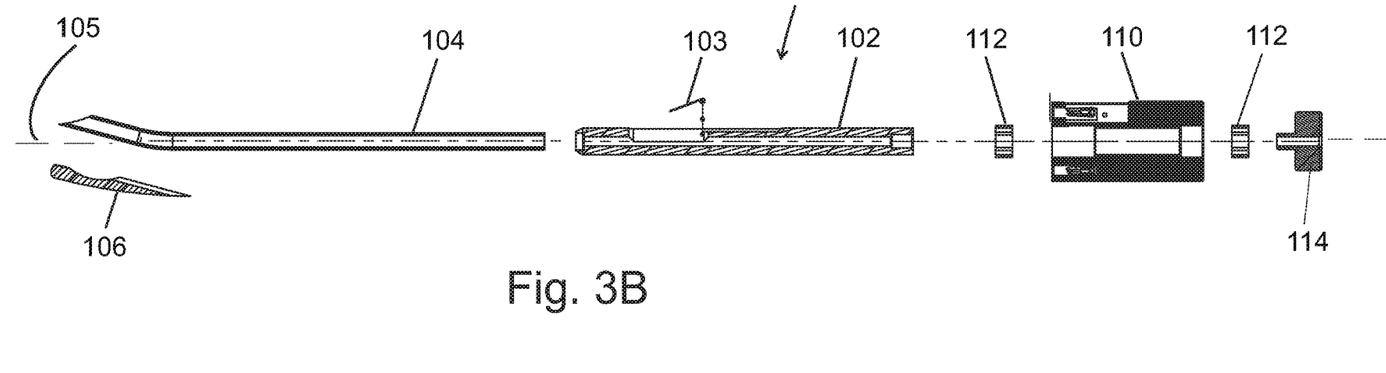

Reference is now made to FIGS. 3A & 3B, which are simplified exploded and sectional exploded views respectively of a tool for labrum repair procedure 100 constructed and operative in accordance with an embodiment of the present invention.

It is seen in FIGS. 3A & 3B that a hollow distal tube portion 102 is adapted to be attached to a proximal tube portion 104, both are adapted to be arranged along a longitudinal axis 105. A guiding element 103 is adapted to be attached to the distal tube portion 102 for guiding insertion of anchors into the distal tube portion 102. A holding member 106 is adapted to be attached to the proximal tube portion 105 for supporting the tissue, for example the labrum, while manipulating various surgical tools at the treatment site.

It is appreciated that proximal tube portion 104 and distal tube portion 102 are alternatively formed as a single integrally made element.

An anchor cassette 110 is adapted to be attached to the distal tube portion 102 and secured thereon using typically two retaining elements 112. A cover 114 is adapted to be partially inserted into the distal end of the anchor cassette 110 for centering surgical tools that are adapted to pass through the tool for labrum repair procedure 100.

Figure 4A:
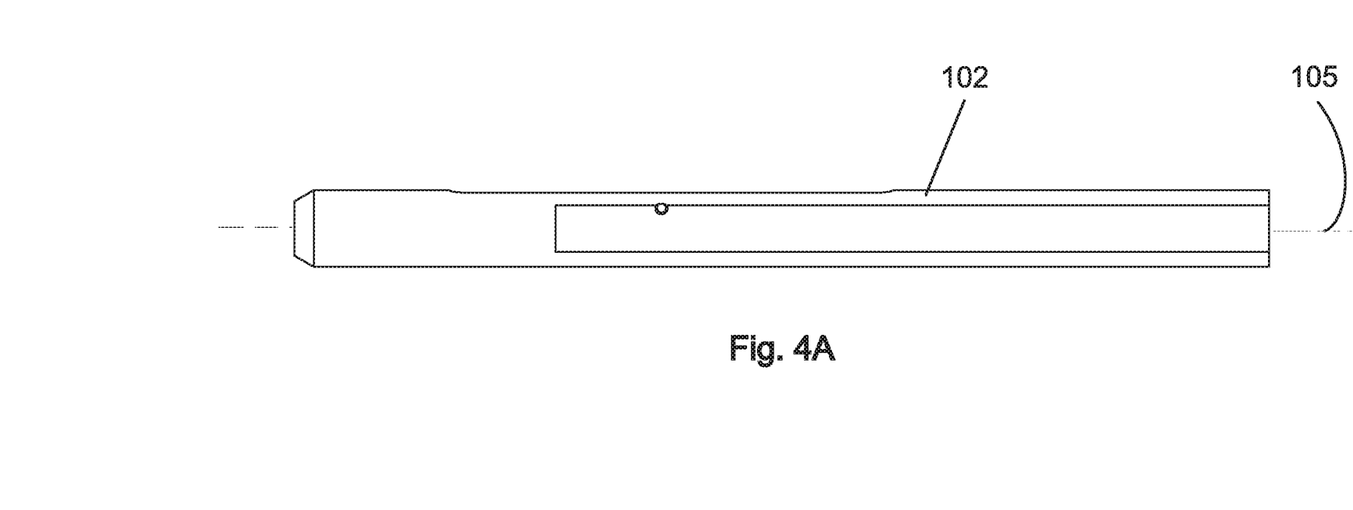
FIGS. 4A & 4B are simplified side and sectional views of a distal tube portion of the tool for labrum repair procedure of FIGS. 3A & 3B.
Figure 4B:
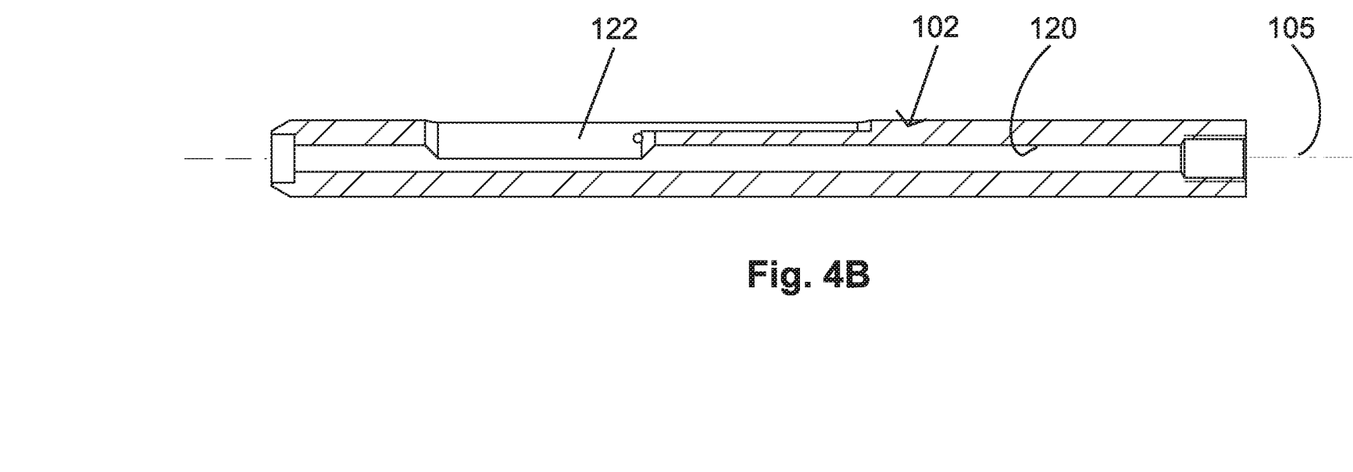

Reference is now made to FIGS. 4A & 4B, which are simplified side and sectional views of a distal tube portion 102 of the tool for labrum repair procedure 100 of FIGS. 3A & 3B.

It is seen in FIGS. 4A & 4B that the distal tube portion 102 is preferably an integrally made element arranged along longitudinal axis 105 and having a longitudinal bore 120 extending therethrough. It is further seen that an opening 122 is formed on the circumference of distal tube portion 102 for insertion of surgical anchors into the longitudinal bore 120.

Figure 5A:
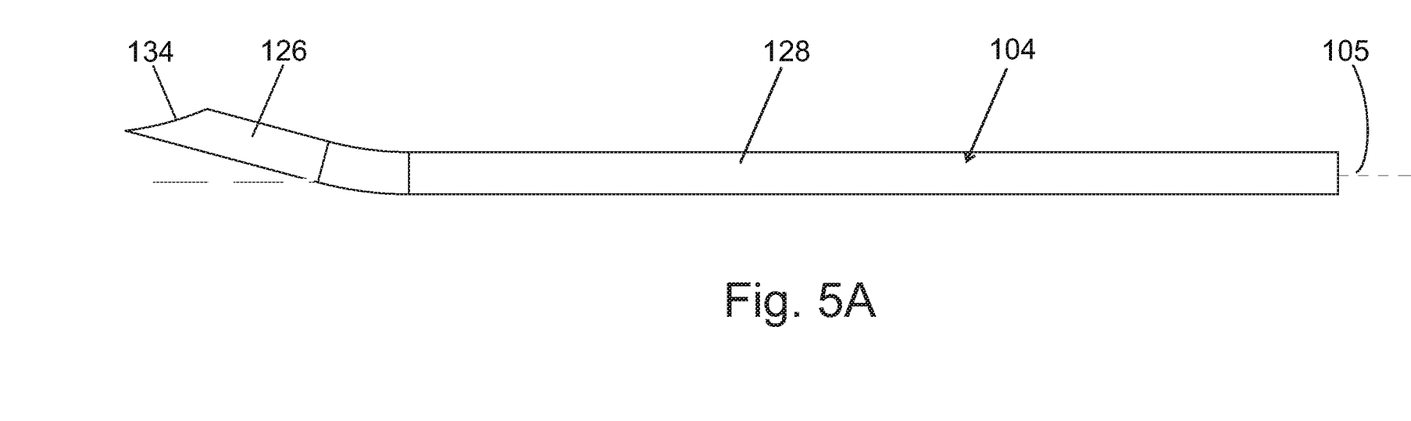
FIGS. 5A & 5B are simplified side and sectional views of a proximal tube portion of the tool for labrum repair procedure of FIGS. 3A & 3B.
Figure 5B:
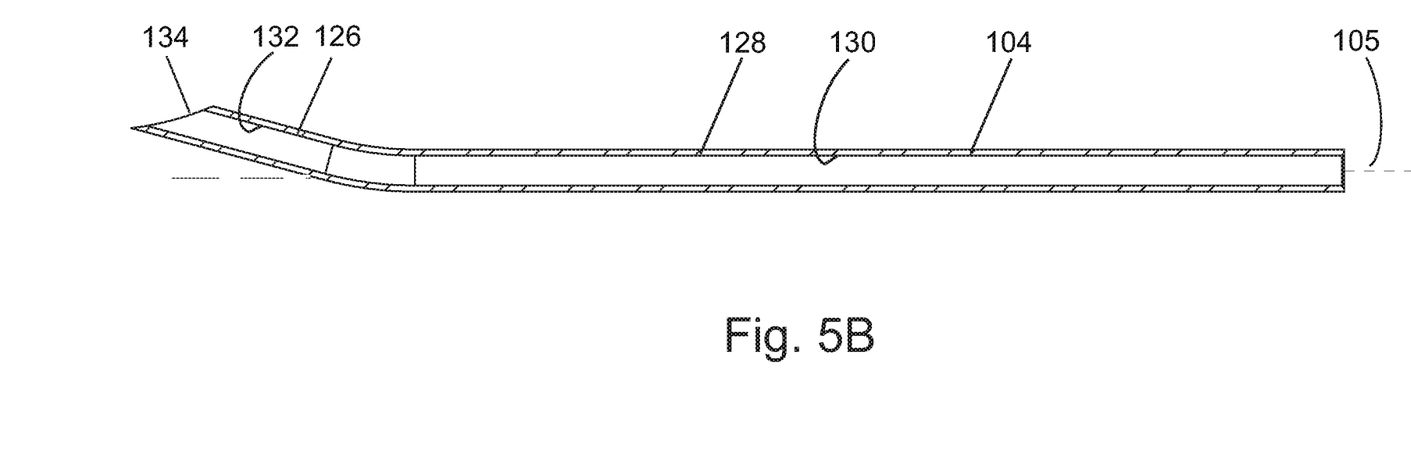

Reference is now made to FIGS. 5A & 5B, which are simplified side and sectional views of a proximal tube portion 102 of the tool for labrum repair procedure 100 of FIGS. 3A&3B.

It is seen in FIGS. 5A & 5B that the proximal tube portion 104 is preferably an integrally made element partially arranged along longitudinal axis 105. A proximal end 126 thereof is preferably arranged at an angle with respect to a main portion 128 of the proximal tube portion 104. A longitudinal bore 130 is formed through main portion 128 and bore 132 is formed through proximal end 126. The proximal end 126 defines a slanted edge 134.

Figure 6:
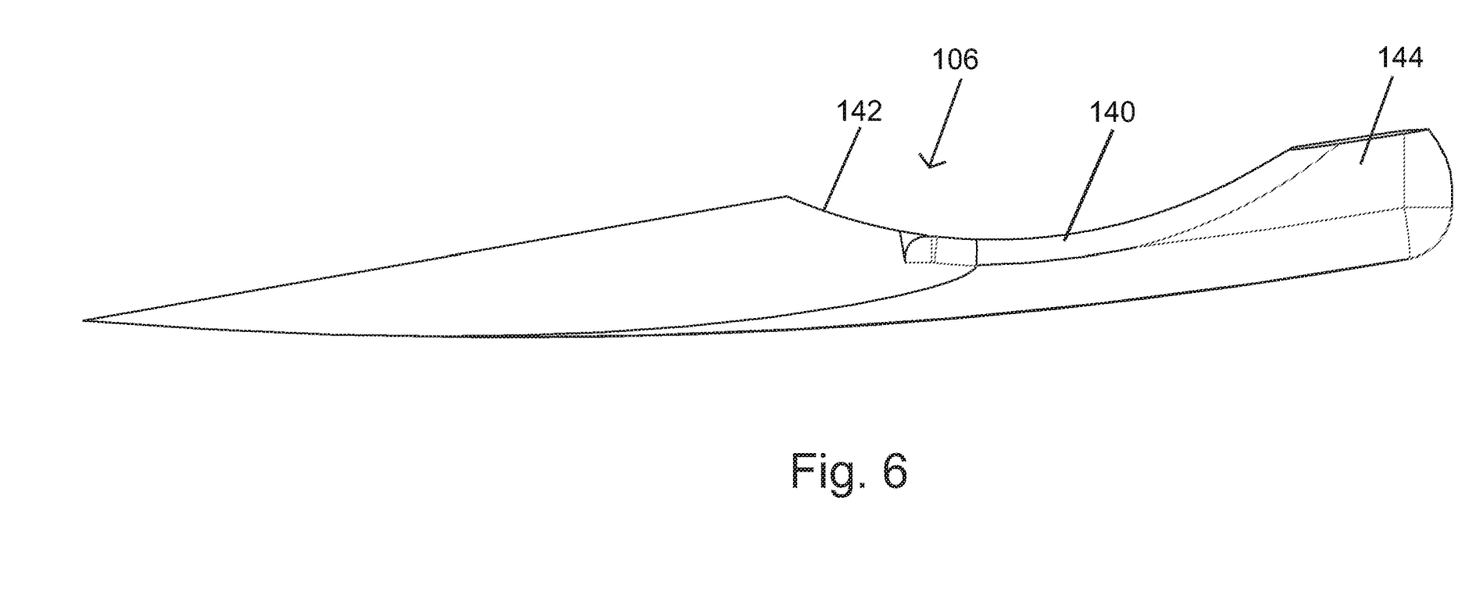
FIG. 6 is a simplified side view of a holding member of the tool for labrum repair procedure of FIGS. 3A & 3B.

Reference is now made to FIG. 6, which is a simplified side view of the holding member 106 of the tool for labrum repair procedure 100 of FIGS. 3A & 3B.

It is seen in FIG. 6 that the holding element 106 is preferably an integrally made element. Holding element 106 preferably has a concave surface 140 and an upwardly facing raised portion 142 disposed proximally thereto for supporting the treated tissue. The distal end 144 of the holding element 106 is adapted to be securely attached to the proximal tube portion 104 of the tool for labrum repair procedure 100.

It is appreciated that the holding element 106 may be rotatably attached to the proximal tube portion 104 of the tool for labrum repair procedure 100.

Figure 7:
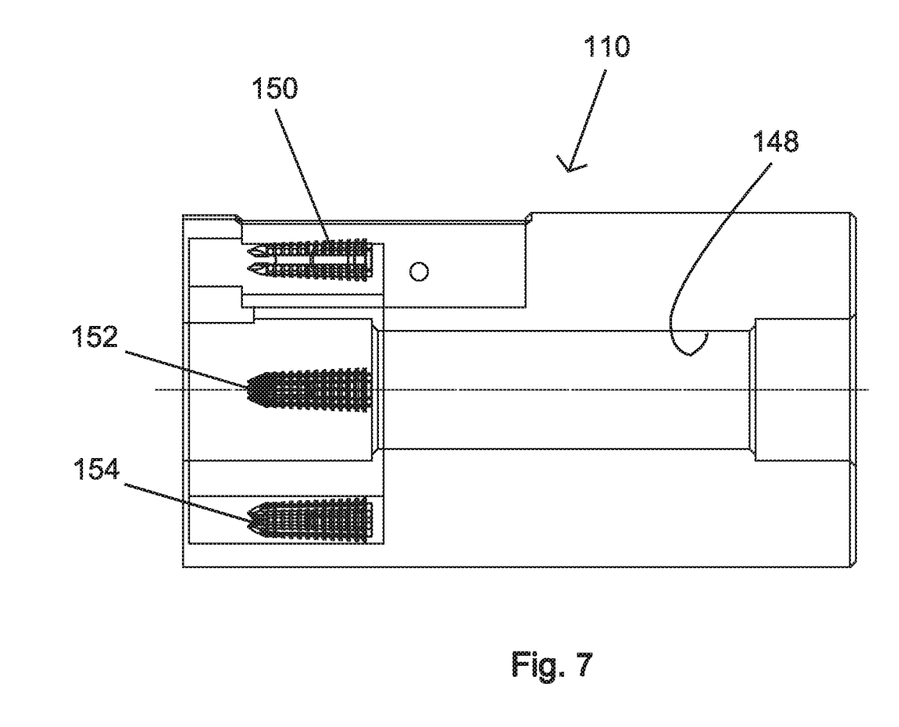
FIG. 7 is a simplified partial cutaway illustration of an anchor cassette adapted for attachment to the tool for labrum repair procedure of FIGS. 3A & 3B.

Reference is now made to FIG. 7, which is a simplified partial cutaway illustration of an anchor cassette 110 adapted for attachment to the tool for labrum repair procedure 100 of FIGS. 3A & 3B.

It is seen that anchor cassette is arranged along longitudinal axis 105 and includes a longitudinal bore 148 adapted for mounting of the anchor cassette onto the distal tube portion 102.

In this particular example shown in FIG. 7, anchors 150, 152 and 154 are disposed within the anchor cassette, alternatively any other number of anchors can be disposed within the anchor cassette and at least two of the anchors are attached by a surgical suture (not shown). Preferably the anchors 150, 152 and 152 are supported by a spring (not shown).

It is a particular feature of an embodiment of the present invention that typically two linked anchors, such as 150 and 152 are disposed within the anchor cassette, the anchors 150 and 152 are attached one to another by a suture. Alternatively, each of the anchors is disposed separately in the anchor cassette 110.

It is appreciated that the anchor cassette is disposable and once anchors are removed therefrom, a new anchor cassette 110 is adapted to be mounted onto the tool for labrum repair procedure 110.

Figure 8A:
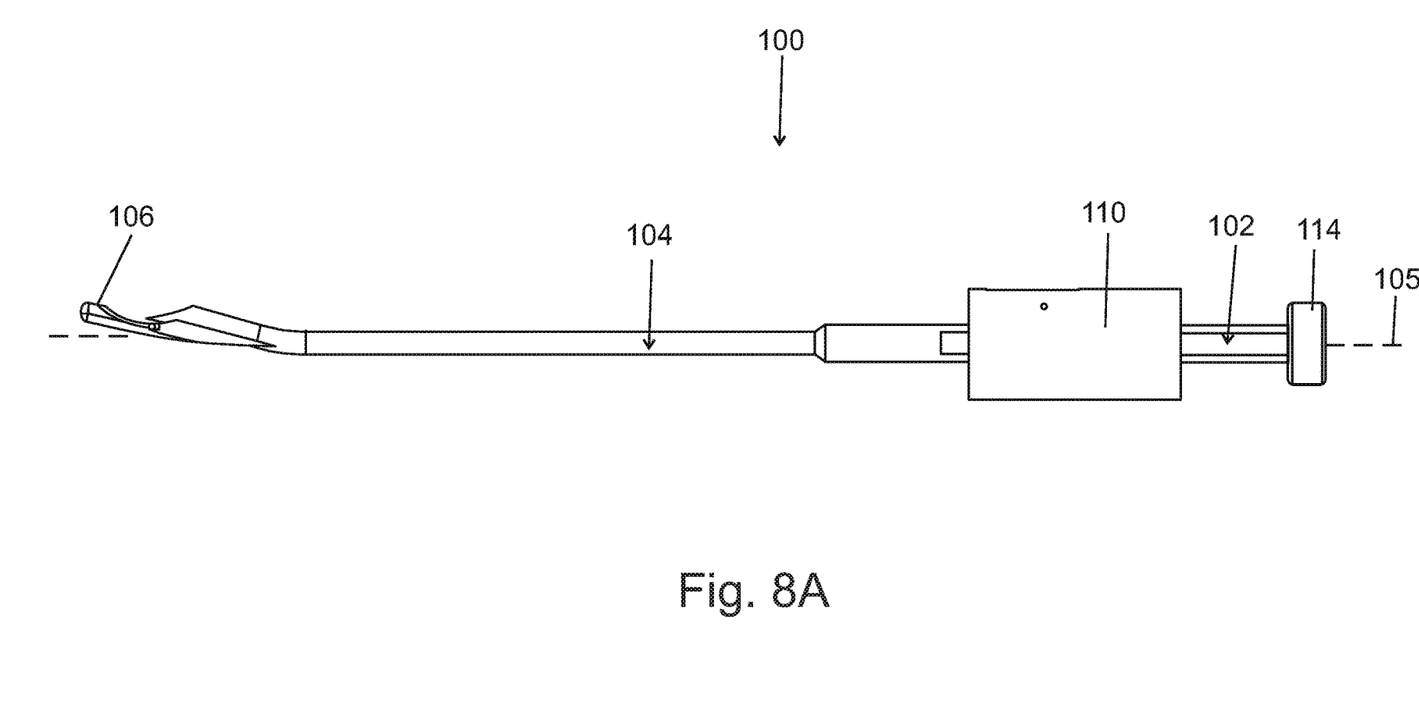
FIGS. 8A & 8B are simplified side and sectional views of the assembled tool for labrum repair procedure of FIGS. 3A & 3B.
Figure 8B:
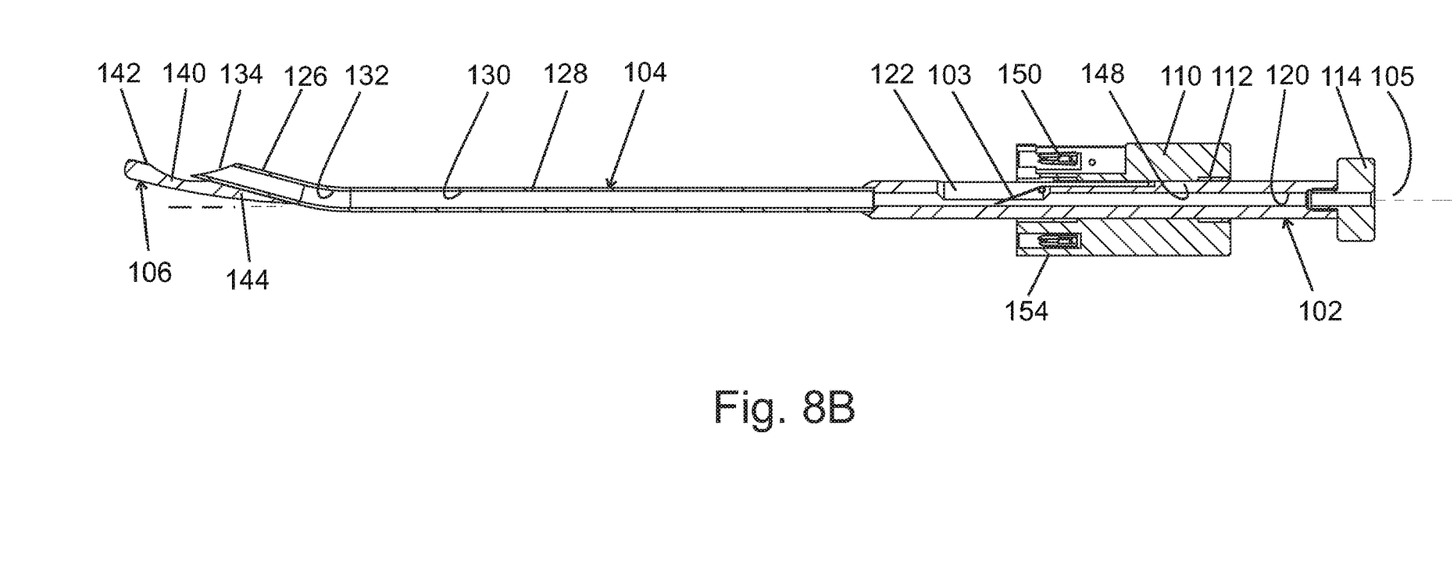

Reference is now made to FIGS. 8A & 8B, which are simplified side and sectional views of the assembled tool for labrum repair procedure 100 of FIGS. 3A & 3B.

It is seen in FIGS. 8A & 8B that distal tube portion 102 is attached to proximal tube portion 104 or integrally made therewith and the holding element 106 is in turn attached to proximal tube portion 104. The holding element 106 can be rotatably adjustable with respect to the proximal tube portion 104, such that the holding portion 106 can be positioned at various angles with respect to the proximal tube portion 104.

The cover 114 is securely attached to the distal end of the distal tube portion 102 for centering surgical tools that are adapted to be entered into the tool 100.

It is a particular feature of an embodiment of the present invention that longitudinal bore 120, bore 130 and bore 132 form a working channel through which surgical tools can be passed and the holding element 106 is integrally formed therewith, so that the soft tissue may be retained and supported by the concave surface 140 and raised portion 142.

The anchor cassette 110 is preferably secured around the distal tube portion 102, such that anchors 150, 152 and 154 are disposed adjacent guiding element 103 and slightly distally thereto. Guiding element 103 is closed when a surgical tool is inserted through the working channel, and once the surgical tool is removed from the working channel, the guiding element 103 is allowed to be opened and at least one of anchors 150, 152 and 154 are released and guided into the working channel defined by bores 120, 130 and 132.

Figure 9:
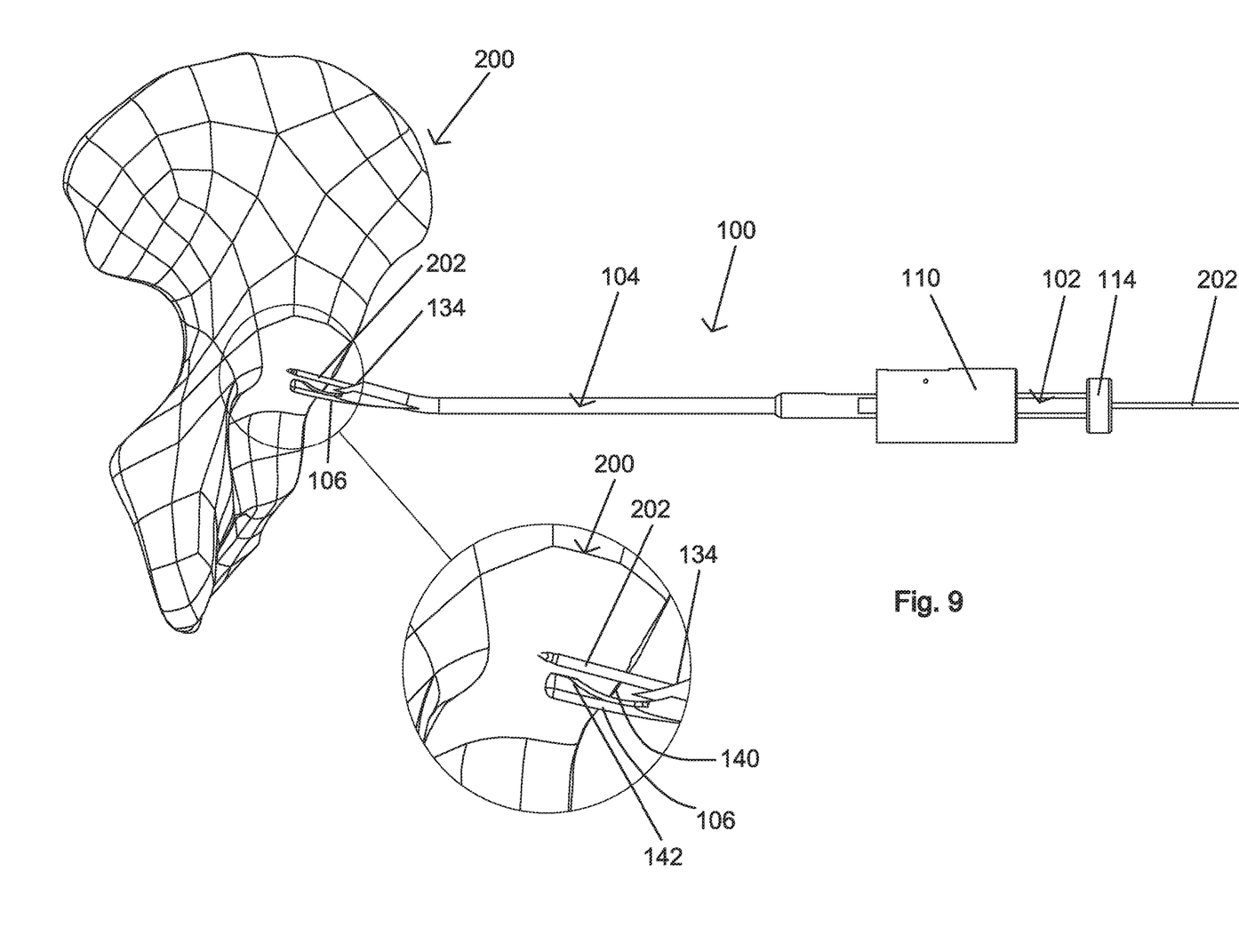
FIG. 9 is a simplified side view illustration and an enlargement of the tool for labrum repair procedure of FIGS. 3A & 3B with a drill, shown within the bone of a patient.

Reference is now made to FIG. 9, which is a simplified side view illustration and an enlargement of the tool for labrum repair procedure 100 of FIGS. 3A & 3B with a drill, shown within the bone of a patient.

It is seen in FIG. 9 that a drill 202, such as a K-wire, is passed through the working channel of the tool for labrum repair procedure 100. The proximal tip of the drill 202 extends through the labrum into the bone 200 of the patient while the holding element 106 supports the labrum.

It is noted that as long as the drill 202 is positioned within the working channel the guiding element 103 is closed and anchors are prevented from being released into the working channel.

Figure 10:
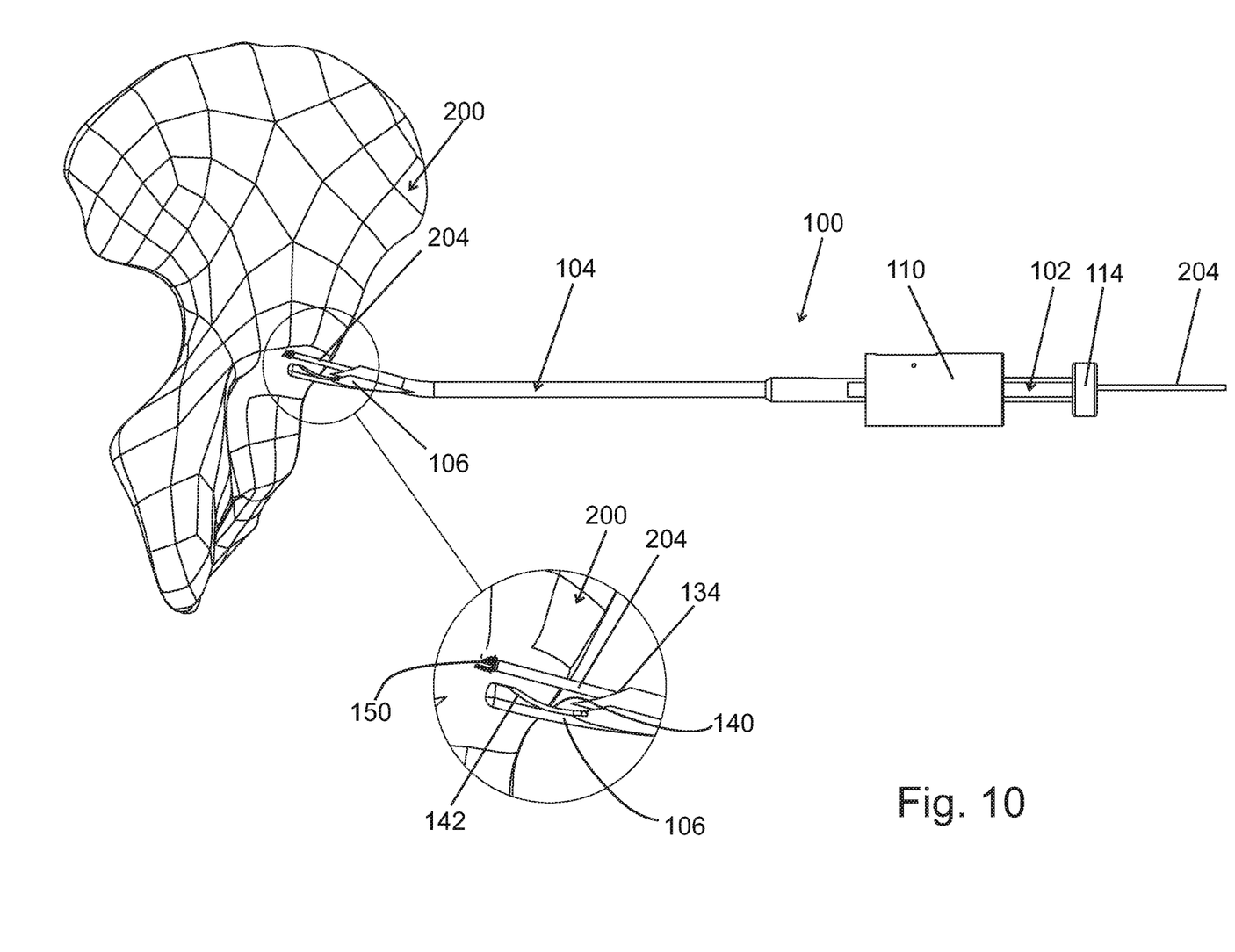
FIG. 10 is a simplified side view illustration and an enlargement of the tool for labrum repair procedure of FIGS. 3A & 3B with a drill, shown within the bone of a patient.

Reference is now made to FIG. 10, which is a simplified side view illustration and an enlargement of the tool for labrum repair procedure 100 of FIGS. 3A & 3B with a pusher, shown within the bone of a patient.

It is seen in FIG. 10 that a guiding element 103 allows releasing of a single or a plurality of anchors, such as anchors 150, 152 and 154 to be released into the working channel and then a pusher 204 is inserted into the working channel and displaced proximally in order to secure the anchors into the bone 200 of the patient while passing through the labrum.

It is appreciated that each of the anchors can be inserted into each drilled bore separately. Alternatively, two anchors or more can be linked by a suture, thus one suture is adapted to be inserted into a first bore and another suture is adapted to be inserted into a second bore and then the suture is tightened to provide for a footprint, providing greater pressure exerted on the labrum, thus attaching the labrum to the rim of the acetabular or the glenoid bone.

It will be appreciated by persons skilled in the art that the present invention is not limited by what has been particularly shown and described hereinabove. Rather the scope of the present invention includes both combinations and subcombinations of various features described hereinabove as well as variations and modifications thereof which are not in the prior art.

What is claimed is:

1. An arthroscopic tool for a labrum repair procedure, comprising:
    a cannulated working channel having a proximal end and a distal end, wherein said working channel proximal end has a terminal edge and a terminal opening through said working channel proximal end, wherein said terminal edge is located entirely at a location proximal with respect to said working channel;
    wherein said working channel has a longitudinal axis along at least a distal portion of said working channel, and wherein said working channel proximal end is arranged at a non-zero angle relative to said longitudinal axis; and
    a holding element located at said proximal end of said working channel, said holding element including at least one supporting surface for simultaneously:
    supporting a labrum; and
    allowing passage of a drill through both the labrum and a bone adjacent the labrum during the arthroscopic labrum repair procedure.

2. An arthroscopic tool for labrum repair procedure in accordance to claim 1, also comprising an anchor cassette adapted to be attached to said working channel.

3. An arthroscopic tool for labrum repair procedure in accordance to claim 2, and wherein said anchor cassette includes at least two anchors, which are linked together by a surgical suture.

4. An arthroscopic tool for labrum repair procedure in accordance with claim 2, wherein said working channel has a longitudinal axis along at least a distal portion of said working channel, and wherein said anchor cassette is arranged along said working channel longitudinal axis.

5. An arthroscopic tool for labrum repair procedure in accordance with claim 2, wherein said anchor cassette is mounted onto said working channel.

6. An arthroscopic tool for labrum repair procedure in accordance with claim 1, wherein said holding element has a distal end adapted to be securely attached to said proximal end of said working channel.

7. An arthroscopic tool for labrum repair procedure in accordance with claim 1, wherein said working channel proximal end defines a slanted edge.

8. An arthroscopic tool for labrum repair procedure in accordance with claim 7, wherein said holding element is adapted to be attached to said proximal end of said working channel at said slanted edge.

9. An arthroscopic tool for labrum repair procedure in accordance with claim 8, wherein said holding element includes an upwardly facing raised portion adapted to support treated tissue during the labrum repair procedure.

10. An arthroscopic tool for labrum repair procedure in accordance with claim 9, wherein said holding element includes a concave surface distal to said upwardly facing raised portion, said concave surface adapted to support the treated tissue during the labrum repair procedure.

11. An arthroscopic tool for labrum repair procedure in accordance with claim 1, wherein said holding element is selectably positionable at various angles with respect to said working channel.

12. An arthroscopic tool for labrum repair procedure in accordance with claim 1, wherein said working channel is adapted for the passage of at least one surgical drill through said working channel.

13. An arthroscopic tool for labrum repair procedure in accordance with claim 12, wherein said holding element is positionable relative to said working channel such that the surgical drill passing through said working channel will pass through a portion of the labrum supported on said at least one supporting surface.

14. An arthroscopic tool for labrum repair procedure in accordance with claim 1, wherein said arthroscopic tool includes a guide attached to a portion of said working channel, said guide adapted to guide insertion of at least one anchor into said portion of said working channel.

15. An arthroscopic tool for labrum repair procedure in accordance with claim 14, wherein said guide has a closed orientation and wherein said working channel is sized and shaped for positioning of a drill inside said working channel when said guide is in said closed orientation.

16. An arthroscopic tool for labrum repair procedure in accordance with claim 15 wherein, when said guide is in said closed orientation, said at least one anchor is prevented from being released into said working channel.

17. An arthroscopic tool for labrum repair procedure in accordance with claim 1, wherein said working channel is sized and shaped for insertion of a pusher into said working channel, said pusher is proximally displaceable to secure at least one anchor into a bone.

18. An arthroscopic tool for labrum repair procedure in accordance with claim 1, wherein said terminal opening has a shape corresponding to a cross-section of said working channel, said cross-section taken through said working channel longitudinal axis, said cross-section taken at angle relative to said working channel proximal end.

19. An arthroscopic tool for labrum repair procedure in accordance with claim 1, wherein a most proximal end of said working channel defines a plane, and wherein said terminal opening defines a surface parallel with the plane.

20. An arthroscopic tool for labrum repair procedure in accordance with claim 1, wherein said holding element allows aligning the labrum and the bone adjacent the labrum.

21. An arthroscopic tool for labrum repair procedure in accordance with claim 1, wherein said holding element is rotatable about said working channel longitudinal axis.

22. An arthroscopic tool for labrum repair procedure in accordance to claim 1, wherein said supporting surface allows passage of the drill through both the labrum and one of:
   an acetabular bone; and
   a glenoid bone.

23. An arthroscopic tool for labrum repair procedure in accordance with claim 1, wherein said tool is used as a working channel for at least one of a drill, a pusher, a suture passer, and a suture cutter.

24. An arthroscopic tool for labrum repair procedure in accordance with claim, 1, said tool including a distal tube portion and an attached proximal tube portion, wherein said working channel extends through said distal tube portion and said proximal tube portion.

25. An arthroscopic tool for a tissue repair procedure in accordance with claim 1, wherein the tissue repair procedure is a labrum repair procedure, said tool including:
   a holding element located at said proximal end of said working channel, said holding element including at least one supporting surface for simultaneously:
   supporting the labrum; and
   allowing passage of a drill through both the labrum and a bone adjacent the labrum during the arthroscopic labrum repair procedure.

26. An arthroscopic tool for a labrum repair procedure, comprising:
   a cannulated working channel having a proximal end and a distal end, wherein said working channel proximal end has a terminal edge and a terminal opening through said working channel proximal end, wherein said terminal edge is located entirely at a location proximal with respect to said working channel;
   wherein said working channel has a longitudinal axis along at least a distal portion of said working channel, and wherein said working channel proximal end is arranged at a non-zero angle relative to said longitudinal axis; and
   a holding element located at said proximal end of said working channel, said holding element including at least one supporting surface for supporting a labrum during the arthroscopic labrum repair procedure;
   wherein said holding element includes an upwardly facing raised portion adapted to support treated tissue during the labrum repair procedure, and wherein said holding element includes a concave surface distal to said upwardly facing raised portion, said concave surface adapted to support the treated tissue during the labrum repair procedure.

27. An arthroscopic tool for a labrum repair procedure, comprising:
   a cannulated working channel having a proximal end and a distal end, wherein said working channel proximal end has a terminal edge and a terminal opening through said working channel proximal end, wherein said terminal edge is located entirely at a location proximal with respect to said working channel;
   wherein said working channel has a longitudinal axis along at least a distal portion of said working channel, and wherein said working channel proximal end is arranged at a non-zero angle relative to said longitudinal axis; and
   a holding element located at said proximal end of said working channel, said holding element including at least one supporting surface for simultaneously:
   supporting a labrum; and
   allowing passage of a drill through both the labrum and a bone adjacent the labrum during the arthroscopic labrum repair procedure;
   wherein said arthroscopic tool also comprises an anchor cassette adapted to be attached to said working channel, and wherein said anchor cassette includes at least two anchors.

28. An arthroscopic tool for labrum repair procedure in accordance with claim 27, wherein said at least two anchors are linked together by a surgical suture.

29. An arthroscopic tool for a labrum repair procedure, comprising:
   a cannulated working channel having a proximal portion with a proximal end and a distal portion, wherein a continuous bore extends through said working channel proximal and distal portions, wherein said working channel proximal end has a terminal edge and a terminal opening through said working channel proximal end, wherein said terminal edge is located entirely at a location proximal with respect to said working channel;
   wherein said working channel has a longitudinal axis along said distal portion of said working channel, wherein said continuous bore includes a distal bore portion formed through said working channel distal portion and a proximal bore portion formed through said working channel proximal portion, and wherein said proximal bore portion is arranged at a non-zero angle relative to said longitudinal axis; and
   a holding element located at said proximal end of said working channel, said holding element including at least one supporting surface for supporting a labrum during the arthroscopic labrum repair procedure.

30. An arthroscopic tool for labrum repair procedure in accordance with claim 29, wherein said holding element includes an upwardly facing raised portion adapted to support treated tissue during the labrum repair procedure, and wherein said holding element includes a concave surface distal to said upwardly facing raised portion, said concave surface adapted to support the treated tissue during the labrum repair procedure.

31. An arthroscopic tool for a labrum repair procedure, comprising:

a cannulated working channel having a proximal end and a distal end, wherein said working channel proximal end has a terminal edge and a terminal opening through said working channel proximal end, wherein said terminal edge is located entirely at a location proximal with respect to said working channel;

wherein said working channel has a longitudinal axis along at least a distal portion of said working channel, and wherein said working channel proximal end is arranged at a non-zero angle relative to said longitudinal axis; and a holding element adapted to be attached to said proximal end of said working channel, said holding element including at least one supporting surface for supporting a labrum during the arthroscopic labrum repair procedure.

32. An arthroscopic tool for a tissue repair procedure, comprising:

a cannulated working channel having a proximal portion with a proximal end and a distal portion, wherein a continuous bore extends through said working channel proximal and distal portions, wherein said working channel proximal end has a terminal edge and a terminal opening through said working channel proximal end, wherein said terminal edge is located entirely at a location proximal with respect to said working channel;

wherein said working channel has a longitudinal axis along said distal portion of said working channel, wherein said continuous bore includes a distal bore portion formed through said working channel distal portion and a proximal bore portion formed through said working channel proximal portion, and wherein said proximal bore portion is arranged at a non-zero angle relative to said longitudinal axis; and wherein said working channel is sized and shaped for insertion of a pusher into said working channel, said pusher is proximally displaceable to secure a plurality of anchors into a bone, said plurality of anchors linked together by a surgical suture.

* * * * *